United States Patent [19]

Brouwer

[11] Patent Number: 5,824,704

[45] Date of Patent: Oct. 20, 1998

[54] ANTI-VIRAL AROMATIC O-ALKYLATED OXIMES, ETHERS AND THIOETHERS

[75] Inventor: Walter Gerhard Brouwer, Guelph, Canada

[73] Assignee: Uniroyal Chemical Co./CIE., Elmira, Canada

[21] Appl. No.: 852,939

[22] Filed: May 8, 1997

Related U.S. Application Data

[63] Continuation-in-part of Ser. No. 346,819, Nov. 30, 1994, Pat. No. 5,663,199.

[51] Int. Cl.$^6$ ............... A61K 31/34; A61K 31/16; C07D 307/02; C07C 327/00

[52] U.S. Cl. ............... 514/471; 514/599; 514/629; 514/433; 514/448; 549/487; 549/72; 549/14; 564/74; 564/192; 564/218

[58] Field of Search ............... 549/487, 72, 14; 514/471, 599, 629, 433, 448

[56] References Cited

U.S. PATENT DOCUMENTS 5,268,389  12/1993  Harrison et al. ............... 514/485
5,663,199   9/1997  Brouwer ............... 514/471

*Primary Examiner*—Deborah C. Lambkin
*Attorney, Agent, or Firm*—Daniel Reitenbach

[57] ABSTRACT

Compounds of the formula

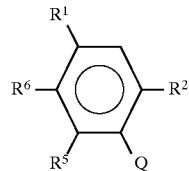

These compounds are useful for inhibiting the growth or replication of retroviruses such as HIV.

16 Claims, No Drawings

ANTI-VIRAL AROMATIC O-ALKYLATED OXIMES, ETHERS AND THIOETHERS

This is a continuation-in-part of U.S. application Ser. No. 08/346,819, filed on Nov. 30, 1994, U.S. Pat. No. 5,663,199.

FIELD OF THE INVENTION

This invention relates to novel aromatic O-alkylated oximes, ethers and thioethers. In particular, this invention relates to novel aromatic O-alkylated oximes, ethers and thioethers useful as anti-viral agents. More particularly, this invention relates to novel aromatic O-alkylated oximes, ethers and thioethers useful as agents against certain retroviruses such as the members of the group of Human Immunodeficiency Viruses (HIV).

BACKGROUND OF THE INVENTION

Retroviruses are viruses whose replication requires the transcription of viral RNA into DNA using the viral reverse transcriptase molecules attached to the viral RNA. This reverse transcription is the opposite of normal transcription which makes RNA from DNA.

Known retroviruses include HIV-1, HIV-2, the herpes family of viruses, HTLV-1 and cytomegalovirus (CMV). HIV, the virus which is presently believed to cause acquired immunodefiency syndrome (AIDS), is considered one of the principle threats to human life and health worldwide.

Various anti-HIV compounds have been proposed as useful in the treatment and prevention of AIDS, e.g., zidovudine (AZT), didanosine (ddI), zalcitabine (ddc), nevirapine, and dextran sulfate. However, none of the proposed compounds have been proven to be totally effective in the treatment or prevention of AIDS. For example, the three currently FDA approved compounds for the treatment of AIDS, i.e., AZT, ddI and ddC, can all cause undesirable side effects in a patient, such as inhibition of bone marrow cell growth, and their effectiveness is limited by virus mutation.

U.S. Pat. No. 5,268,389 describes certain thiocarboxylate ester compounds useful for inhibiting the growth or replication of HIV.

It is the purpose of this invention to provide novel aromatic O-alkylated oximes, ethers and thioethers, useful as anti-viral agents.

It is also the purpose of this invention to provide a method for inhibiting or preventing the growth or replication of human immunodeficiency viruses using the novel aromatic O-alkylated oximes, ethers and thioethers.

Finally, it is also the purpose of this invention to provide compositions useful for inhibiting or preventing the growth or replication of human immunodeficiency viruses, comprising the novel aromatic O-alkylated oximes, ethers and thioethers.

DESCRIPTION OF THE INVENTION

This invention relates to a compound of the formula

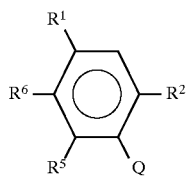
(I)

wherein Q is

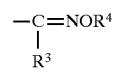

or —XR';

X is oxygen or sulphur;

$R^1$ is hydrogen, halogen, $C_1$–$C_4$ alkyl or $C_1$–$C_4$ alkoxy;

$R^2$ is hydrogen, halogen, $C_1$–$C_4$ alkyl, $C_1$–$C_4$ alkoxy, $C_3$–$C_4$ alkenyloxy, $C_3$–$C_4$ alkynyloxy, mono-, di- or trihalomethyl, trifuluoromethoxy, $C_1$–$C_4$ alkylthio, $C_3$–$C_4$ branched alkylthio, nitro, or cyano;

$R^3$ is hydrogen or $C_1$–$C_4$ alkyl;

$R^4$ is $C_3$–$C_6$ alkenyl, $C_3$–$C_6$ alkynyl, $C_1$–$C_8$ haloalkyl, $C_1$–$C_8$ alkoxyalkyl, $C_1$–$C_8$ alkylthioalkyl, $C_1$–$C_8$ hydroxyalkyl, $C_1$–$C_8$ acyloxyalkyl, $C_1$–$C_8$ aroyloxyalkyl, $C_1$–$C_8$ carboxyalkyl, $C_1$–$C_8$ alkylcarboxyalkyl, $C_6$–$C_{12}$ arylcarboxyalkyl, $C_1$–$C_8$ aminoalkyl, $C_1$–$C_8$ alkylaminoalkyl, $C_1$–$C_8$ dialkylaminoalkyl, $C_1$–$C_8$ trialkylsilylalkyl, wherein each of the aforementioned alkyl moieties may be straight-chain or branched; $C_3$–$C_8$ cycloalkyl, $C_1$–$C_6$ alkylphenyl, $C_7$–$C_{12}$ arylalkyl, $C_7$–$C_{12}$ alkarylalkyl, or heterocyclylalkyl, wherein the heterocyclic moiety is morpholinyl, piperidinyl, pyrrolidinyl, piperazinyl, oxiranyl, oxetanyl, furanyl, tetrahydropyranyl or tetrahydrofuranyl;

R' is $C_1$–$C_8$ haloalkyl, $C_1$–$C_8$ haloalkenyl, $C_1$–$C_8$ alkoxyalkyl, $C_1$–$C_8$ alkylthioalkyl, $C_1$–$C_8$ hydroxyalkyl, $C_1$–$C_8$ acyloxyalkyl, $C_1$–$C_8$ aroyloxyalkyl, $C_1$–$C_8$ aminoalkyl, $C_1$–$C_8$ alkylaminoalkyl, $C_1$–$C_8$ dialkylaminoalkyl, $C_1$–$C_8$ trialkylsilylalkyl, wherein each of the aforementioned alkyl moieties may be straight-chain or branched; $C_1$–$C_6$ alkylphenyl, $C_7$–$C_{12}$ arylalkyl, $C_7$–$C_{12}$ alkarylalkyl, or heterocyclylalkyl, wherein the heterocyclic moiety is morpholinyl, piperidinyl, pyrrolidinyl, piperazinyl, oxiranyl, oxetanyl, furanyl, tetrahydropyranyl or tetrahydrofuranyl;

$R^5$ is hydrogen, halo, methyl, mono-, di- or trihalomethyl;

$R^6$ is

1) $R^Z$ —NH—, wherein $R^Z$ is

wherein $R^a$ and $R^b$ are independently hydrogen or $C_1$–$C_6$ alkyl; and $Z^1$ is O or S; or

wherein $Z^2$ is O or S; and $R^A$ is:

a) fully unsaturated, partially or fully reduced or substituted oxathiinyl, furanyl, dithiinyl, dioxinyl, thienyl, thiazolyl, oxazolyl, isoxazolyl, isothiazolyl, thiadiazolyl, pyrazolyl, pyrrolyl, imidazolyl, pyranyl, oxathiazinyl, oxadiazolyl, or indolyl;

b) substituted or unsubstituted, linear or branched $C_1$–$C_8$ alkyl, $C_2$–$C_8$ alkenyl, $C_2$–$C_8$ alkynyl, $C_1$–$C_8$ alkoxy, $C_2$–$C_8$ alkenyloxy, $C_2$–$C_8$ alkynloxy, or $C_1$–$C_8$ mono- or di-alkylamino; $C_3$–$C_7$ cycloalkyl, $C_3$–$C_7$ cycloalkyl $C_1$–$C_6$ alkyl, $C_3$–$C_7$ cycloalkenyl, unsubstituted or substituted by $C_1$–$C_6$ alkyl or $C_7$–$C_8$ phenylalkyl; or c) aryl, aralkyl, aryloxyalkyl, or cycloalkylaryloxy wherein each alkyl moiety contains from 1 to 10 carbon atoms and each aryl moiety is naphthyl, phenyl or phenyl substituted by one or more halo, $C_1$–$C_8$ alkyl, carboxyl, $C_1$–$C_8$ haloalkyl, $C_1$–$C_8$ alkylthio, phenyl, nitro, amino, $C_1$–$C_8$ alkoxycarbonylamino, hydroxyl, acetyl, acetyloxy, phenoxy, $C_1$–$C_8$ alkoxycarbonyl or $C_1$–$C_8$ alkylcarbonyl;

(d) $R^7$—W—, wherein

W is O, NH or $NR^f$ wherein $R^f$ is $C_1$–$C_4$ alkyl; and $R^7$ is linear or branched, unsubstituted or halo-substituted $C_1$–$C_8$ alkyl, $C_2$–$C_8$ alkenyl, $C_2$–$C_8$ alknyl, $C_3$–$C_7$ cycloalkyl $C_1$–$C_6$ alkyl, $C_3$–$C_7$ cycloalkenyl unsubstituted or substituted by $C_1$–$C_6$ alkyl, unsubstituted phenyl or phenyl substituted by halo, $C_1$–$C_6$ alkyl, $C_1$–$C_6$ alkoxy, carboxyl, $C_1$–$C_8$ alkythio, phenyl, nitro, amino, hydroxyl, acetyl, acetyloxy, phenoxy, $C_1$–$C_8$ alkoxycarbonyl, or $C_1$–$C_8$ alkylcarbonyl; furanylalkyl, tetrahydrofuranylalkyl, oxetanylalkyl, or oxiranylalkyl;

e) $R^8$ —$W^1$ —$R^e$, wherein
$R^e$ is a linear or a branched $C_1$–$C_6$ alkylidene;
$W^1$ is O or S; and
$R^8$ is linear or branched $C_1$–$C_4$ alkyl;

f) $R^9$ $R^{10}$—N—$R^e$, wherein
$R^e$ is as defined above; and $R^9$ and $R^{10}$ are independently linear or branched $C_1$–$C_4$ alkyl;

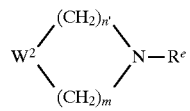

wherein
$R^e$ is as defined above;
$W^2$ is O, S, NH, $NR^{11}$ or $CR^{12}R^{13}$; wherein $R^{11}$ is linear or branched $C_{1-4}$ alkyl; $R^{12}$ and $R^{13}$ are independently hydrogen or linear or branched $C_1$–$C_4$ alkyl; and
n' and m are independently 1, 2 or 3;

h) $R^{14}$ —$O_2$—C—$R^e$, wherein
$R^e$ is as defined above; and $R^{14}$ is linear or branched $C_1$–$C_6$ alkyl, $C_3$–$C_6$ alkenyl, or $C_3$–$C_6$ alkynyl; or $C_3$–$C_7$ cycloalkyl, $C_3$–$C_7$ cycloalkyl $C_1$–$C_6$ alkyl, or $C_3$–$C_7$ cycloalkenyl, unsubstituted or substituted by $C_1$–$C_6$ alkyl;

i) U—$R^e$—, wherein
$R^e$ is as defined above; U is hydroxyl, acyloxy, aryloxy, arylsulphonyloxy, nitro, cyano or trimethylsilyl;

j) 1-adamantyl, 2-adamantyl or bornyl;

k) $Ar^1$—$R^e$—, wherein
$R^e$ is as defined above; and
$Ar^1$ is phenyl or phenyl substituted independently with one to three halogen, mono-, di- or tri- halomethyl, nitro, $C_1$–$C_4$ alkyl, $C_3$–$C_4$ alkenyl, $C_1$–$C_4$ alkyloxy, $C_3$–$C_4$ alkenyloxy, or $C_3$–$C_4$ alkynyloxy.

Preferred compounds are those compounds wherein $R^6$ is

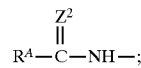

$Z^2$ is O or S; and
$R^A$ is
a) fully unsaturated, partially or fully reduced or substituted oxathiinyl, furanyl, dithiinyl, dioxinyl, thienyl, thiazoyl, oxazoyl, isoxazoyl, isothiazoyl, thiadiazolyl, pyrazolyl, pyrrolyl, pyranyl, oxathiazinyl, or oxadiazolyl;
b) linear or branched $C_1$–$C_8$ alkyl, $C_3$–$C_8$ alkenyl, $C_3$–$C_8$ alkynyl, $C_1$–$C_8$ alkoxy, $C_3$–$C_8$ alkenyloxy, $C_3$–$C_8$ alkynloxy, or $C_1$–$C_8$ mono- or di- alkylamino; $C_3$–$C_6$ cycloalkyl or $C_3$–$C_6$ cycloalkenyl;
c) phenyl or phenyl substituted by one or more halo, $C_1$–$C_8$ alkyl, $C_1$–$C_8$ haloalkyl, $C_1$–$C_8$ alkylthio, phenyl, amino, hydroxyl, carboxyl, acetyl, acetyloxy, $C_1$–$C_8$ alkoxycarbonyl, $C_1$–$C_8$ alkylcarbonyl or phenoxy; $C_7$–$C_8$ phenylalkyl or $C_7$–$C_8$ phenoxyalkyl.

More preferred are those compounds wherein $R^A$ is
a) dihydro-3-oxathiinyl, furanyl, dihydrofuranyl, thienyl, pyrrolyl, dihydro-2-dithiinyl, or dihydro-2-dioxinyl, which can be substituted by one to three $C_1$–$C_4$ alkyl or $C_1$–$C_4$ alkoxyalkyl groups;
b) linear or branched $C_1$–$C_8$ alkyl, $C_2$–$C_8$ alkenyl, $C_3$–$C_8$ alkynyl, $C_1$–$C_8$ alkoxy, $C_3$–$C_8$ alkenyloxy, $C_3$–$C_8$ alkynyloxy or $C_1$–$C_8$ mono- or di-alkylamino; $C_3$–$C_6$ cycloalkyloxy or $C_3$–$C_6$ cycloalkenyloxy; or
c) phenyl or phenyl substituted by one or more halo, $C_1$–$C_8$ alkyl, $C_1$–$C_8$ haloalkyl, $C_1$–$C_8$ alkylthio, carboxyl, amino, $C_1$–$C_8$ alkoxycarbonyl, hydroxyl, $C_1$–$C_8$ alkylcarbonyl, phenyl or phenoxy.

Particularly preferred are those compounds wherein $R^6$

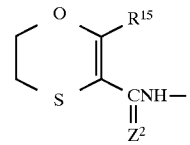

$Z^2$ is O or S;
$R^1$ is hydrogen; fluoro; or methyl;
$R^2$ is hydrogen, chloro, fluoro, or methyl;
$R^3$ is hydrogen or methyl;
$R^4$ is cyclopentyl or cyclohexyl;
$R^5$ is hydrogen; and
$R^{15}$ is methyl, ethyl or propyl.

Additionally preferred compounds are the furan, thiophene and pyrrole derivatives of the compound of formula I wherein $R^6$ is:

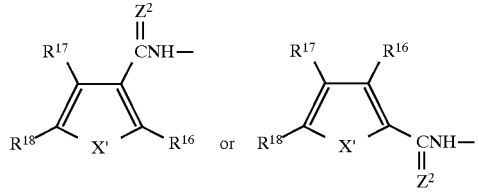

$Z^2$ is O or S;
$X^1$ is O, S, NH or N-methyl,
$R^{16}$ is hydrogen, methyl, ethyl, 1,1-dimethylethyl, fluoro, chloro, carboxyl, acetamido, cyano, $C_1$–$C_6$ alkylthio, $C_1$–$C_6$ haloalkoxy, $C_1$–$C_6$ acyloxy, ($C_1$–$C_6$ alkoxy)carbonyl, or ($C_1$–$C_6$ alkyl)carbonyl; and
$R^{17}$ and $R^{18}$ are independently hydrogen or methyl.

More preferred furan, thiophene and pyrrole derivatives are those wherein $R^1$, $R^3$ and $R^5$ are hydrogen, $R^2$ is halogen, $R^4$ is $C_3$–$C_6$ alkenyl or $C_3$–$C_6$ alkynyl, which can be linear, branched or cyclic, and $Z^2$ is S.

Also preferred are the compounds of formula I wherein $R^6$ is:

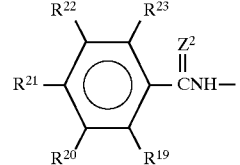

$Z^2$ is O or S;
$R^{19}$, $R^{20}$, $R^{21}$, and $R^{22}$ are independently hydrogen or halogen, preferably hydrogen; and $R^{23}$ is hydrogen, halogen, $C_1$–$C_4$ alkyl, $C_1$–$C_4$ alkoxy, mono, di- or tri-haloalkoxy, $C_1$–$C_4$ haloalkyl, $C_1$–$C_4$ alkylthio, amino, $C_1$–$C_8$ alkylcarbonylamino, hydroxyl, acetyl, acetyloxy, or acetylamino, preferably hydrogen, methyl, ethyl, chloro, iodo, amino, bromo, fluoro, methylthio, methoxy, difluoromethoxy, or hydroxy.

Also preferred as compounds of this invention are the derivatives of acyclic carboxamides or carbamates of the compound of formula I wherein X, $Z^2$, $R^1$, $R^2$, $R^3$, $R^4$ and $R^5$ are as recited above for formula I and $R^6$ is

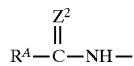

wherein $R^A$ is a linear or branched $C_3$–$C_6$ alkyl, $C_3$–$C_6$ alkenyl, $C_1$–$C_6$ alkoxy, $C_3$–$C_6$ alkenyloxy, $C_3$–$C_6$ alkynyloxy, $C_3$–$C_6$ mono- or di-alkylamino, or $C_3$–$C_6$ alkynyl; phenyl, $C_7$–$C_8$ phenylalkyl, $C_7$–$C_8$ phenoxyalkyl, $C_3$–$C_7$ cycloalkyl, or $C_3$–$C_7$ cycloalkenyl.

More preferred compounds are the compounds of formula I wherein R— is hydrogen or fluoro; $R^4$ is $C_3$–$C_6$ alkenyl or $C_3$–$C_6$ alkynyl, which may be linear, branched or cyclic; $R^6$ is

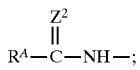

$R^A$ is a linear or branched $C_3$–$C_6$ alkyl, $C_3$–$C_6$ alkenyl, $C_3$–$C_6$ alkynyl, $C_3$–$C_6$ alkoxy, $C_3$–$C_6$ alkenyloxy or $C_3$–$C_6$ alkynyloxy; $C_7$–$C_8$ phenylalkyl, $C_7$–$C_8$ phenoxyalkyl, $C_3$-$C_6$ cycloalkyl, or $C_3$–$C_7$ cycloalkenyl.

Especially preferred compounds of this invention are the compounds of formula I wherein $R^1$–$R^5$ are hydrogen; $R^4$ is $C_3$–$C_6$ alkenyl or $C_3$–$C_6$ alkynyl, which may be linear, branched or cyclic; $R^6$ is

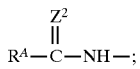

$R^A$ is a linear or branched $C_3$–$C_6$ alkyl, $C_3$–$C_6$ alkoxy, $C_3$–$C_6$ alkenyloxy, $C_3$–$C_6$ alkynyloxy, $C_3$–$C_6$ cycloalkyl, or $C_3$–$C_6$ cycloalkenyl.

Further preferred compounds of this invention are the compounds of formula I wherein $R^1$ and $R^5$ are hydrogen; $R^2$ is chloro or $C_1$–$C_4$ alkoxy; $R^6$ is

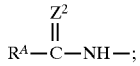

$R^A$ is dihydro-3-oxathiinyl, furanyl, thienyl, substituted by one to three $C_1$–$C_4$ alkyl groups; Q is XR' wherein R' is $C_1$–$C_4$ mono-haloalkyl, $C_1$–$C_4$ di-haloalkyl, $C_1$–$C_4$ mono-haloalkenyl, or $C_1$–$C_4$ di-haloalkenyl.

The compounds of this invention are useful for the inhibition of the growth or replication of retroviruses, particularly human immunodeficiency viruses such HIV-1, in vitro and in vivo. The compounds are useful in the therapeutic or prophylactic treatment of diseases caused by retroviruses, such as acquired immune deficiency syndrome or an HIV infection in a human or other mammal.

It is intended that the scope of this invention encompass all isomers, including positional or stereoisomers, of any compound of formula I exhibiting isomerism. It is also intended that any novel processes or intermediates for synthesizing said compounds be included within the scope of this invention.

GENERAL SYNTHETIC METHODS

Compounds of formula

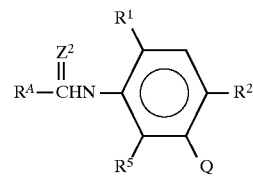

wherein $Z^2$ is O and $R^A$ is oxathiinyl, furanyl, thienyl, pyrrolyl, other heterocyclyl, or substituted phenyl, can be prepared from the appropriate carboxylic acid, $R^A$—COOH, and an aniline derivative, i.e;

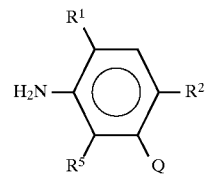

by employing one of the methods known in the art of amide bond formation. For example, the carboxylic acid can be converted to an acid halide, such as the acid chloride, $R^A$COCl, which can then be reacted with the aniline derivative to form the amide. The amide forming reaction is carried out in an appropriate solvent, such as methylene chloride, toluene, methyl ethyl ketone, tetrahydrofuran, dimethylformamide or acetonitrile, at a temperature of about 0° C. to about 100° C.

It is usually preferable to carry out the reaction in the presence of a base, such as triethylamine or pyridine. Other reactive derivatives of the carboxylic acid can be employed: for example the anhydride of the carboxylic acid or a mixed anhydride, such as alkoxycarbonyloxy derivative, can be reacted with the aniline derivative. Alternatively, the carboxylic acid and aniline derivative can be reacted directly in the presence of a condensing agent such as dicyclohexylcarbodiimide to form the amide.

The aniline derivatives can be prepared by reduction of the corresponding nitro compounds by well-known methods, for example with hydrogen and a catalyst, such as Raney nickel or platinum, or with a metal-acid combination, such as iron or tin and hydrochloric or acetic acid. Oxime ethers are made from the corresponding aldehyde by conventional methods. An exception is in the preparation of tertiary o-alkyl oximes which are made by the action of an unsubstituted oxime and a tertiary alcoholic ester under acid catalysis in a suitable solvent such as THF, dioxane or DME. A suitable acid catalyst would be hydrochloric, sulphuric or perchloric acid.

Other compounds of this invention in which $R^A$ is an alkoxy can be prepared by reacting the appropriate aniline derivative with an alkoxycarbonyl chloride, under conditions essentially similar to those used for reaction of an acid chloride with the aniline derivative. They can also be prepared by reacting the appropriate isocyanate derivative with an alcohol. The isocyanate can be prepared by reacting the aniline derivative or a suitable salt thereof, such as the hydrochloride, with phosgene or a phosgene substitute, such as trichloromethyl chloroformate.

Compounds of this invention wherein $R^A$ is alkoxy and $Z^2$ is sulphur can be similarly prepared using alkoxy thiocarbonyl chloride under conditions described above or from the appropriate isothiocyanate derivative and an alcohol.

Thiocarboxaniliides of this invention wherein $Z^2$ is S and $R^A$ is furanyl, thienyl, pyrrolyl, other heterocyclyl or substituted phenyl, can be prepared starting from the corresponding amide and reacting it with a sulfurating agent such as Lawesson's reagent or phosphorus pentasulphide in a suitable solvent such as toluene, xylene, DME, pyridine, or the like.

The following examples are provided to illustrate the synthesis of the compounds of the present invention.

EXAMPLE I

The following Tables 1a and 1b list representative compounds that were prepared using the methods described above.

TABLE 1a

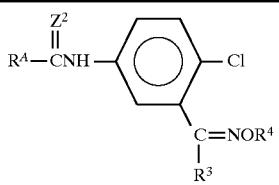

| No. | $R^A$ | $Z^2$ | $R^3$ | $R^4$ | mp °C. |
|---|---|---|---|---|---|
| 1 | 2-CH$_3$-3-Furanyl | O | H | CH$_2$C≡CH | 135–136 |
| 2 | " | S | H | CH$_2$CH=CH$_2$ | 88–89 |
| 3 | " | S | H | CH$_2$C≡CH | 79–80 |
| 4 | " | S | H | CH$_2$C$_6$H$_5$ | 131–133 |
| 5 | " | S | H | CH$_2$CO$_2$C(CH$_3$)$_3$ | 130–131 |
| 6 | " | S | R | C$_5$H$_9$(cyclo) | 73–75 |

TABLE 1b

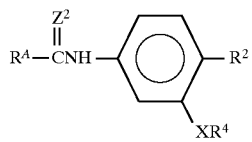

| No. | $R^A$ | $Z^2$ | X | $R^2$ | $R^4$ | mp °C. |
|---|---|---|---|---|---|---|
| 7 | (CH$_3$)$_2$CHO | S | O | Cl | CHF$_2$ | 110–115 |
| 8 | " | S | O | Cl | COCH(CH$_3$)$_2$ | 89–91 |
| 9 | " | S | O | Cl | CH$_2$COCH$_3$ | 104–108 |
| 10 | " | S | O | Cl | CH$_2$C(=NOH)CH$_3$ | 101–105 |

IN VITRO SCREENING RESULTS

Representative compounds of this invention were tested for anti-viral activity by subjecting them to standard National Cancer Institute ("NCI") in vitro screening procedures. Two blanks were run with each test. The NCI test for agents active against HIV is designed to detect agents acting at any stage of the virus reproduction cycle.

In the test assay, small amounts of HIV are added to T4 lymphocyte cells. The assay measures the amount of T4 lymphocytes "killed" by HIV cytolysis. Since a complete cycle of viral reproduction is necessary to "kill" the T4 lymphocyte cells, agents that interfere with viral reproduction will protect the cells from cytolysis.

The NCI system is automated in several features to accomodate large numbers of candidate agents and is generally designed to detect anti-HIV activity. Compounds that degenerate or are rapidly metabolized in the culture conditions do not show activity in this screen. All tests are compared with at least one positive (AZT-treated) control done at the same time under identical conditions.

The Test Procedure

1) The test compound was dissolved in dimethyl sulfoxide and diluted 1:100 in cell culture medium before serial half-log$_{10}$ dilutions were prepared. T4 lymphocytes (CEM cell line) were then added to the cell culture medium, and, finally, after a brief interval, HIV-1 was added, resulting in a 1:200 final dilution of the test compound. Uninfected cells in the cell culture medium containing the test compound (i.e., minus HIV-1) were used as a toxicity control, and infected cells in the cell culture medium without the test compound and uninfected cells in the cell culture medium without the test compound, were used as basic controls.

2) The cultures were incubated at 37° C. in a 5% carbon dioxide atmosphere for 6 days.

3) The tetrazolium salt, XTT, was added to all wells, and the cultures were then incubated to allow formazan color development by viable cells.

4) Individual wells were analyzed spectrophotometrically to quantitate formazan production, and were also viewed microscopically for detection of viable cells and confirmation of protective activity.

5) Virus-infected cells exposed to the test compound were compared with noninfected cells exposed to the test compound, and with other appropriate controls (infected cells not exposed to the test compound and noninfected cells not exposed to the test compound, wells containing only the test compound in the cell culture medium, and so on) on the same plate. These are the first and second blanks described below.

6) Data were reviewed in comparison with other tests done at the same time and a determination concerning activity was made. In the first blank, HIV and T4 lymphocytes in cell culture medium, were incubated together to measure the infectivity of the virus. The viability of the cells was measured after holding for six or seven days. In an "effective" test, most cells were infected before the holding period was complete.

In the second blank, the T4 lymphocytes in cell culture medium and the test compound (with no HIV-1) were incubated together to measure the toxicity of the drug to the cellline. The viability of the cells was measured as a function of concentration of the compound, after incubation for seven days. The concentration of the test compound that results in 50% inhibition of cell growth is defined as its IC$_{50}$.

Finally, the protective effects of the test compounds were measured. Each cell culture and test compound were incubated with the virus and the viability of the cells was measured as a function of compound concentration after incubation for six or seven days. The concentration of the test compound that results in 50% "control," i.e., a 50% reduction of the viral cytopathic effect, is defined as its EC$_{50}$. The therapeutic index TI$_{50}$ was calculated as IC$_{50}$/EC$_{50}$.

Concentrations of test compounds required for between 20 and 50% reduction of the viral cytopathic effect can also be determined. Such compounds are classified as moderately active. Compounds with less than 20% control are considered inactive.

The compounds were tested to determine their reduction of HIV cytopathic effect on the human cell line CEM. Tests were done by innoculating these cell lines in-well (IW), i.e., the test compound and CEM cells were mixed on a test plate and the virus was added a short time later.

Screening Data for Test Compound Exhibiting Inhibition of HIV

The preceding protocol was carried out with all of the compounds described above in the Examples, all of which showed some significant activity in at least one of the tests.

The test results (molar) for all the tested compounds are shown in Table 2 as $IC_{50}$, $EC_{50}$ and $TI_{50}$.

TABLE 2

| Compound | $IC_{50}(M)$ | $EC_{50}(M)$ | $TI_{50}$ |
|---|---|---|---|
| 1 | $1.60 \times 10^{-5}$ | $3.30 \times 10^{-6}$ | 5 |
|   | $1.80 \times 10^{-5}$ | $3.50 \times 10^{-6}$ | 5 |
|   | $>2.30 \times 10^{-5}$ | $3.90 \times 10^{-6}$ | >6 |
|   | $>2.30 \times 10^{-5}$ | $3.70 \times 10^{-6}$ | >6 |
| 2 | $>1.60 \times 10^{-5}$ | $1.10 \times 10^{-8}$ | >1400 |
|   | $>1.60 \times 10^{-5}$ | $2.00 \times 10^{-8}$ | >770 |
|   | $>1.60 \times 10^{-5}$ | $4.50 \times 10^{-8}$ | >340 |
|   | $>1.60 \times 10^{-5}$ | $1.20 \times 10^{-8}$ | >1300 |
| 3 | $1.60 \times 10^{-5}$ | $4.70 \times 10^{-8}$ | 340 |
|   | $1.60 \times 10^{-5}$ | $3.80 \times 10^{-8}$ | 440 |
|   | $>2.20 \times 10^{-5}$ | $1.30 \times 10^{-7}$ | >170 |
|   | $2.10 \times 10^{-5}$ | $1.10 \times 10^{-7}$ | 190 |
| 4 | $>7.10 \times 10^{-6}$ | $1.00 \times 10^{-6}$ | >7 |
|   | $>7.10 \times 10^{-6}$ | $1.60 \times 10^{-6}$ | >4 |
|   | $>7.10 \times 10^{-6}$ | $1.30 \times 10^{-6}$ | >5 |
|   | $>7.10 \times 10^{-6}$ | $1.10 \times 10^{-6}$ | >7 |
| 5 | $>2.40 \times 10^{-5}$ | $2.00 \times 10^{-5}$ | >1 |
|   | $>2.40 \times 10^{-5}$ | — | — |
|   | $1.90 \times 10^{-5}$ | $4.40 \times 10^{-6}$ | 4 |
|   | $2.30 \times 10^{-5}$ | — | — |
| 6 | $>1.40 \times 10^{-5}$ | $2.50 \times 10^{-7}$ | >58 |
|   | $>1.40 \times 10^{-5}$ | $2.40 \times 10^{-7}$ | >59 |
|   | $>1.40 \times 10^{-5}$ | $1.80 \times 10^{-7}$ | >78 |
|   | $>1.40 \times 10^{-5}$ | $8.40 \times 10^{-8}$ | >170 |
| 7 | $3.47 \times 10^{-5}$ | $2.62 \times 10^{-6}$ | 13 |
|   | $4.64 \times 10^{-5}$ | $8.37 \times 10^{-6}$ | 6 |
|   | $3.22 \times 10^{-5}$ | — | — |
|   | $3.33 \times 10^{-5}$ | $5.78 \times 10^{-6}$ | 6 |
| 8 | $5.56 \times 10^{-5}$ | — | — |
|   | $5.13 \times 10^{-5}$ | $2.80 \times 10^{-5}$ | 2 |
|   | $4.17 \times 10^{-5}$ | $2.54 \times 10^{-5}$ | 2 |
|   | $4.75 \times 10^{-5}$ | $1.81 \times 10^{-5}$ | 3 |
| 9 | $7.70 \times 10^{-5}$ | $2.70 \times 10^{-6}$ | 28 |
|   | $>1.20 \times 10^{-4}$ | $2.00 \times 10^{-6}$ | >61 |
|   | $>1.20 \times 10^{-4}$ | $4.60 \times 10^{-6}$ | >26 |
|   | $>1.20 \times 10^{-4}$ | $1.10 \times 10^{-6}$ | >110 |
|   | $1.20 \times 10^{-4}$ | $3.30 \times 10^{-6}$ | 36 |
| 10 | — | $9.7 \times 10^{-8}$ | — |
|    | — | $8.8 \times 10^{-8}$ | — |
|    | — | $2.0 \times 10^{-7}$ | — |
|    | — | $1.6 \times 10^{-7}$ | — |

EXAMPLE II

The following Table 3 lists representative compounds 11–27 prepared according to the methods described above in Example I.

TABLE 3

$$R^A-\overset{\overset{Z^2}{\|}}{C}NH-\underset{XR'}{\bigcirc}-R^2$$

| No. | $R^A$ | $Z^2$ | X | $R^2$ | $R'$ |
|---|---|---|---|---|---|
| 11 | 2-methyl-3-thienyl | S | O | CN | 2-chloro-2-propenyl |
| 12 | 2-methyl-3-furanyl | S | O | Cl | " |
| 13 | " | S | O | $CH_3$ | " |
| 14 | " | S | O | Cl | 3,3-dichloro-2-propenyl |
| 15 | 5,6-dihydro-2-methyl-1,4-oxathiin-3-yl | O | O | Cl | " |
| 16 | 2-methyl-3-furanyl | S | S | Cl | " |
| 17 | " | O | S | Cl | " |
| 18 | " | O | O | Cl | 3-chloro-2-butenyl |
| 19 | " | O | O | $OCH_3$ | 3,3-dichloro-2-propenyl |
| 20 | 2-methyl-3-thienyl | O | O | Cl | " |

TABLE 3-continued $$R^A-\overset{\overset{Z^2}{\|}}{C}NH-\underset{XR'}{\bigcirc}-R^2$$

| No. | $R^A$ | $Z^2$ | X | $R^2$ | $R'$ |
|---|---|---|---|---|---|
| 21 | " | S | O | Cl | " |
| 22 | 2-methyl-3-furanyl | S | O | Cl | 3-chloro-2-butenyl |
| 23 | 5,6-dihydro-2-methyl-1,4-oxathiin-3-yl | S | O | $OCH_3$ | 3,3-dichloro-2-propenyl |
| 24 | 2-methyl-3-thienyl | S | O | $OCH_3$ | " |
| 25 | 5,6-dihydro-2-methyl-1,4-oxathiin-3-yl | O | O | $OCH_3$ | " |
| 26 | 2-methyl-3-furanyl | S | O | $OCH_3$ | " |
| 27 | " | S | O | Cl | 3-(trifluoro-methyl)-2-butenyl (E) |

IN VITRO SCREENING

Cells and Viruses

Human lymphocyte CEM cells were obtained from the American Type Culture Collection and grown in RPMI 1640 medium supplemented with 10% (v/v) inactivated fetal calf serum (Gibco), 2 mM L-glutamine (Flow Laboratories), and 0.075% (v/v) NaHCO3 (Flow Laboratories). Cells were subcultured every 3 to 4 days.

HIV-1(III$_B$) was kindly provided by R. C. Gallo and M. Popovic (National Cancer Institute, Bethesda, Md.). The selection and characterization of the HIV-1 RT mutant strains were done as follows: HIV-1/100-Ile ("100-Ile") was selected for resistance against TIBO R82150 as described in Balzarini et al, Virology 192: 246–253 (1993); HIV-1/103-Asn ("103-Asn") was selected for resistance against TIBO R82913 as described in Balzarini et al, Virology 192: 246–253 (1993); HIV-1/106-Ala ("106-Ala") was selected for resistance against nevirapine as described in Balzarini et al, J. Virol. 67: 5353–5359 (1993); HIV-1/Lys-138 ("Lys-138") was selected for resistance against TSAO-m$^3$T as described in Balzarini et al, Virology 192: 246–253 (1993) and Balzarini et al, Proc. Nat. Acad. Sci. USA 90: 6952–6956 (1993); HIV-1/181-Cys ("181-Cys") was selected for resistance against pyridinone L-697,661 as described in Balzarini et al, Virology 192: 246–253 (1993); and HIV-1/188-His ("188-His") was selected for resistance against HEPT as described in Balzarini et al, Mol. Pharmocol. 44: 694–701 (1993). 188-His was then further converted to HIV-1/188-Leu("188-Leu") upon further passage in cell culture in the absence of the HEPT.

Antiviral activity of the test compounds in cell cultures

CEM cells were suspended at ≈300,000 cells per ml of culture medium and infected with CEM cells were suspended at ≈300,000 cells per ml of culture medium and infected with approximately 100 50% cell culture infective doses of HIV-III$_B$ or one of the HIV-1 RT mutant strains described above. Then 100 μl of the infected cell suspensions was added to 200 μl microtiter plate wells containing 100 μl of appropriate serial (5-fold) dilutions of the test compounds. The inhibitory effect of the test compounds on HIV-1 induced syncytium formation in CEM cells was examined microscopically on day 4 post infection. The 50% effective concentration ($EC_{50}$) was defined as the test compound concentration that inhibits syncytium formation in the HIV-1-infected cell cultures by 50%.

TABLE 4

Antiviral Activity of Compounds 11–26

| Cmpd. | HIV-1 ($III_B$) | 138-Lys | 181-Cys | 106-Ala | 100-Ile | 103-Asn | 188-Leu |
|---|---|---|---|---|---|---|---|
| 11 | 0.03 | 0.13 | 0.44 | 0.2 | 0.2 | 0.4 | 2.0 |
| 12 | 0.047 | 0.26 | 1.07 | 0.51 | 0.7 | 0.65 | 2.0 |
| 13 | 0.09 | 0.6 | 1.47 | 0.67 | 0.95 | 0.75 | 2.0 |
| 14 | 0.0085 | 0.04 | 0.16 | 0.055 | 0.14 | 0.28 | 2.0 |
| 15 | 1.2 | 2.0 | 2.0 | 2.0 | 2.0 | 2.0 | 2.0 |
| 16 | 0.005 | 0.03 | 0.13 | 0.025 | 0.023 | 0.08 | 2.0 |
| 17 | 0.093 | 0.68 | 2.0 | 0.8 | 0.93 | 2.0 | 2.0 |
| 18 | 0.045 | 0.32 | 0.65 | 0.15 | 0.7 | 2.5 | 10.0 |
| 19 | 0.25 | 10.0 | 8.0 | 2.0 | 5.0 | 10.0 | 10.0 |
| 20 | 0.09 | 0.95 | 2.5 | 1.2 | 0.53 | 2.0 | 2.0 |
| 21 | 0.007 | 0.075 | 0.23 | 0.065 | 0.065 | 0.4 | 2.0 |
| 22 | 0.003 | 0.008 | 0.043 | 0.012 | 0.04 | 0.09 | 0.9 |
| 23 | 0.27 | 3.5 | 2.0 | 2.0 | 1.8 | 2.5 | 2.0 |
| 24 | 0.005 | 0.13 | 0.13 | 0.09 | 0.09 | 1.6 | 2.0 |
| 25 | 4.0 | 10.0 | 10.0 | 10.0 | 10.0 | 10.0 | 10.0 |
| 26 | 0.012 | 0.05 | 0.25 | 0.077 | 0.075 | 1.6 | 10.0 |

[a] 50% effective concentration (i.e., compound concentration required to inhibit virus-induced cytopathicity by 50%)

What is claimed is:

1. A compound of the formula

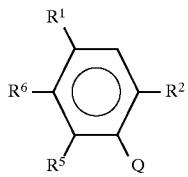

wherein Q is

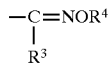

or —XR';

X is oxygen or sulphur;

$R^1$ is hydrogen, halogen, $C_1$–$C_4$ alkyl or $C_1$–$C_4$ alkoxy;

$R^2$ is hydrogen, halogen, $C_1$–$C_4$ alkyl, $C_1$–$C_4$ alkoxy, $C_3$–$C_4$ alkenyloxy, $C_3$–$C_4$ alkynyloxy, mono-, di- or trihalomethyl, trifuluoromethoxy, $C_1$–$C_4$ alkylthio, $C_3$–$C_4$ branched alkylthio, nitro, or cyano;

$R^3$ is hydrogen or $C_1$–$C_4$ alkyl;

$R^4$ is heterocyclylalkyl, wherein the heterocyclic moiety is morpholinyl, piperidinyl, pyrrolidinyl, piperazinyl, oxiranyl, oxetanyl, furanyl, tetrahydropyranyl or tetrahydrofuranyl;

R' is $C_1$–$C_8$ haloalkyl, $C_1$–$C_8$ haloalkenyl, $C_1$–$C_8$ alkoxyalkyl, $C_1$–$C_8$ alkylthioalkyl, $C_1$–$C_8$ hydroxyalkyl, $C_1$–$C_8$ acyloxyalkyl, $C_1$–$C_8$ aroyloxyalkyl, $C_1$–$C_8$ aminoalkyl, $C_1$–$C_8$ alkylaminoalkyl, $C_1$–$C_8$ dialkylaminoalkyl, $C_1$–$C_8$ trialkylsilylalkyl, wherein each of the aforementioned alkyl moieties may be straight-chain or branched; $C_1$–$C_6$ alkylphenyl, $C_7$–$C_{12}$ arylalkyl, $C_7$–$C_{12}$ alkarylalkyl, or heterocyclylalkyl, wherein the heterocyclic moiety is morpholinyl, piperidinyl, pyrrolidinyl, piperazinyl, oxiranyl, oxetanyl, furanyl, tetrahydropyranyl or tetrahydrofuranyl;

$R^5$ is hydrogen, halo, methyl, mono-, di- or trihalomethyl; and $R^6$ is

1) $R^Z$ —NH—, wherein $R^Z$ is

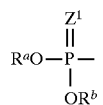 A)

wherein $R^a$ and $R^b$ are independently hydrogen or $C_1$–$C_6$ alkyl; and $Z^1$ is O or S;

 B)

wherein $Z^2$ is O or S; and $R^A$ is:

a) fully unsaturated, partially or fully reduced or substituted oxathiinyl, furanyl, dithiinyl, dioxinyl, thienyl, thiazolyl, oxazolyl, isoxazolyl, isothiazolyl, thiadiazolyl, pyrazolyl, pyrrolyl, imidazolyl, pyranyl, oxathiazinyl, oxadiazolyl, or indolyl;

b) substituted or unsubstituted, linear or branched $C_1$–$C_8$ alkyl, $C_3$–$C_8$ alkenyl, $C_3$–$C_8$ alkynyl, $C_1$–$C_8$ alkoxy, $C_3$–$C_8$ alkenyloxy, $C_3$–$C_8$ alkynyloxy, or $C_1$–$C_8$ mono- or di-alkylamino; $C_3$–$C_7$ cycloalkyl, $C_3$–$C_8$ cycloalkyloxy, $C_3$–$C_8$ cycloalkylalkoxy, $C_3$–$C_7$ cycloalkyl $C_1$–$C_6$ alkyl, $C_3$–$C_7$ cycloalkenyl, unsubstituted or substituted by $C_1$–$C_6$ alkyl or $C_7$–$C_8$ phenylalkyl; or c) aryl, aralkyl, aryloxyalkyl, or cycloalkylaryloxy wherein each alkyl moiety contains from 1 to 10 carbon atoms and each aryl moiety is naphthyl, phenyl or phenyl substituted by one or more halo, $C_1$–$C_8$ alkyl, carboxyl, $C_1$–$C_8$ haloalkyl, $C_1$–$C_8$ alkylthio, phenyl, nitro, amino, $C_1$–$C_8$ alkoxycarbonylamino, hydroxyl, acetyl, acetyloxy, phenoxy, $C_1$–$C_8$ alkoxycarbonyl or $C_1$–$C_8$ alkylcarbonyl:

(d) $R^7$ —W—, wherein
W is O, NH or $NR^f$ wherein $R^f$ is $C_1$–$C_4$ alkyl; and
$R^7$ is linear or branched, unsubstituted or halo-substituted $C_1$–$C_8$ alkyl, $C_3$–$C_8$ alkenyl, $C_3$–$C_8$ alknyl, $C_3$–$C_7$ cycloalkyl $C_1$–$C_6$ alkyl, $C_3$–$C_7$ cycloalkenyl unsubstituted or substituted by $C_1$–$C_6$ alkyl, unsubstituted phenyl or phenyl substituted by halo, $C_1$–$C_6$ alkyl, $C_1$–$C_6$ alkoxy, carboxyl, $C_1$–$C_8$ alkythio, phenyl, nitro, amino, hydroxyl, acetyl, acetyloxy, phenoxy, $C_1$–$C_8$ alkoxycarbonyl, or $C_1$–$C_8$ alkylcarbonyl; furanylalkyl, tetrahydrofuranylalkyl, oxetanylalkyl, or oxiranylalkyl;

e) $R^8$ —W—$R^e$, wherein
$R^e$ is a linear or a branched $C_1$–$C_6$ alkylidene;
$W^1$ is O or S; and
$R^8$ is linear or branched $C_1$–$C_4$ alkyl;

f) $R^9 R^{10}$ —N —R , wherein
$R^e$ is as defined above; and
$R^9$ and $R^{10}$ are independently linear or branched $C_1$–$C_4$ alkyl;

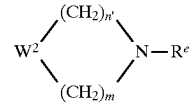

wherein
$R^e$ is as defined above;
$W^2$ is O, S, NH, $NR^{11}$ or $CR^{12}R^{13}$; wherein $R^{11}$ is linear or branched $C_1$–$C_4$ alkyl; $R^{12}$ and $R^{13}$ are independently hydrogen or linear or branched $C_1$–$C_4$ alkyl; and

13 n' and m are independently 1, 2 or 3;
h) $R^{14}$—$O_2$—$C$—$R^e$, wherein
$R^e$ is as defined above; and
$R^{14}$ is linear or branched $C_1$–$C_6$ alkyl, $C_3$–$C_6$ alkenyl, or $C_3$–$C_6$ alkynyl; or $C_3$–$C_7$ cycloalkyl, $C_3$–$C_7$ cycloalkyl $C_1$–$C_6$ alkyl, or $C_3$–$C_7$ cycloalkenyl, unsubstituted or substituted by $C_1$–$C_6$ alkyl;
i) U—$R^e$—, wherein
$R^e$ is as defined above; U is hydroxyl, acyloxy, aryloxy, arylsulphonyloxy, nitro, cyano or trimethylsilyl;
j) 1-adamantyl, 2-adamantyl or bornyl;
k) $Ar^1$ —$R^e$—, wherein
$R^e$ is as defined above; and
$Ar^1$ is phenyl or phenyl substituted independently with one to three halogen, mono-, di- or tri- halomethyl, nitro, $C_1$–$C_4$ alkyl, $C_3$–$C_4$ alkenyl, $C_1$–$C_4$ alkyloxy, $C_3$–$C_4$ alkenyloxy, or $C_3$–$C_4$ alkynyloxy.

2. A compound as recited in claim 1 wherein $R^6$ is

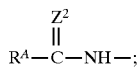

$Z^2$ is O or S; and
$R^A$ is
a) fully unsaturated, partially or fully reduced or substituted oxathiinyl, furanyl, dithiinyl, dioxinyl, thienyl, thiazoyl, oxazoyl, isoxazoyl, isothiazoyl, thiadiazolyl, pyrazolyl, pyrrolyl, pyranyl, oxathiazinyl, or oxadiazolyl;
b) linear or branched $C_1$–$C_8$ alkyl, $C_3$–$C_8$ alkenyl, $C_3$–$C_8$ alkynyl, $C_1$–$C_8$ alkoxy, $C_3$–$C_8$ alkenyloxy, $C_3$–$C_8$ alkynyloxy, or $C_1$–$C_8$ mono- or di- alkylamino; $C_3$–$C_6$ cycloalkyl or $C_3$–$C_6$ cycloalkenyl;
c) phenyl or phenyl substituted by one or more halo, $C_1$–$C_8$ alkyl, $C_1$–$C_8$ haloalkyl, $C_1$–$C_8$ alkylthio, phenyl, amino, hydroxyl, carboxyl, acetyl, acetyloxy, $C_1$–$C_8$ alkoxycarbonyl, $C_1$–$C_8$ alkylcarbonyl or phenoxy; $C_7$–$C_8$ phenylalkyl or $C_7$–$C_8$ phenoxyalkyl.

3. A compound as recited in claim 2 wherein $R^A$ is
a) dihydro-3-oxathiinyl, furanyl, dihydrofuranyl, thienyl, pyrrolyl, dihydro-2-dithiinyl, or dihydro-2-dioxinyl, which can be substituted by one to three $C_1$–$C_4$ alkyl or $C_1$–$C_4$ alkoxyalkyl groups;
b) linear or branched $C_1$–$C_8$ alkyl, $C_3$–$C_8$ alkenyl, $C_3$–$C_8$ alkynyl, $C_1$–$C_8$, alkoxy, $C_1$–$C_8$ mono- or di-alkylamino, $C_3$–$C_6$ cycloalkyl or $C_3$–$C_6$ cycloalkenyl; or
c) phenyl or phenyl substituted by one or more halo, $C_1$–$C_8$ alkyl, $C_1$–$C_8$ haloalkyl, $C_1$–$C_8$ alkylthio, carboxyl, amino, $C_1$–$C_8$ alkoxycarbonyl, hydroxyl, $C_1$–$C_8$ alkylcarbonyl, phenyl or phenoxy.

4. A compound as recited in claim 3 wherein $R^6$ is

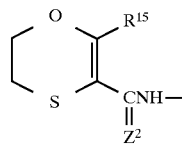

$Z^2$ is O or S;
$R^1$ is hydrogen; fluoro; or methyl;
$R^2$ is hydrogen, chloro, fluoro, or methyl;
$R^3$ is hydrogen or methyl;
$R^5$ is hydrogen; and
$R^{15}$ is methyl, ethyl or propyl.

14

5. A compound as recited in claim 2 wherein $R^6$ is:

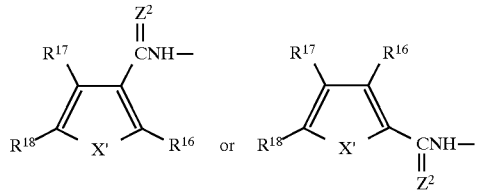

$Z^2$ is O or S;
$X^1$ is O or S;
$R^{16}$ is hydrogen, methyl, ethyl, 1,1-dimethylethyl, fluoro, chloro, carboxyl, acetamido, cyano, $C_1$–$C_6$ alkylthio, $C_1$–$C_6$ haloalkoxy, $C_1$–$C_6$ acyloxy, ($C_1$–$C_6$ alkoxy) carbonyl, or ($C_1$–$C_6$ alkyl)carbonyl; and
$R^{17}$ and $R^{18}$ are independently hydrogen or methyl.

6. A compound as recited in claim 5 wherein $R^1$, $R^3$ and $R^5$ are hydrogen, $R^2$ is halogen, and $R^{16}$ is hydrogen, methyl, ethyl or 1,1-dimethylethyl.

7. A compound as recited in claim 2 wherein $R^6$ is:

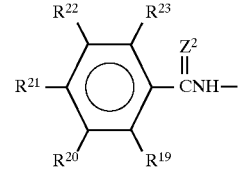

$Z^2$ is O or S;
$R^9$, $R^{20}$, and $R^{22}$ are independently hydrogen or halogen; and
$R^{23}$ is hydrogen, halogen, $C_1$–$C_4$ alkyl, $C_1$–$C_4$ alkoxy, mono-, di- or tri-haloalkoxy, $C_1$–$C_4$ haloalkyl, $C_1$–$C_4$ alkylthio, amino, $C_1$–$C_8$ alkylcarbonylamino, hydroxyl, acetyl, acetyloxy, or acetylamino.

8. A compound as recited in claim 2 wherein $R^A$ is a linear or branched $C_3$–$C_6$ alkyl, $C_3$–$C_6$ alkenyl, $C_3$–$C_6$ alkynyl, $C_3$–$C_6$ alkoxy, or $C_1$–$C_6$ mono- or di-alkylamino; phenyl, $C_7$–$C_8$ phenylalkyl, $C_7$–$C_8$ phenoxyalkyl, $C_3$–$C_7$ cycloalkyl, or $C_3$–$C_7$ cycloalkenyl.

9. A compound as recited in claim 2 wherein Q is —$CR^3$=$NOR^4$, $R^A$ is $C_1$–$C_4$ alkoxy, phenyl, or dihydro-3-oxathiinyl, furanyl, dihydrofuranyl or thienyl substituted by one to three methyl or ethyl groups, $R^1$ is H, $R^2$ is Cl, $R^3$ is H or methyl, and $R^5$ is H.

10. A compound as recited in claim 9 wherein $R^A$ is $C_1$–$C_4$ alkoxy, $Z^2$ is S, and $R^3$ is H.

11. A compound as recited in claim 9 wherein $R^A$ is 2-methyl-3-furanyl, $Z^2$ is S, and $R^3$ is H.

12. A compound as recited in claim 2 wherein Q is —XR', $R^A$ is furanyl, thienyl or dihydro-3-oxathiinyl substituted by one to three methyl or ethyl groups; $R^2$ is Cl or methoxy; and R' is $C_1$–$C_4$ di-haloalkyl, $C_1$–$C_4$ di-haloalkenyl, $C_1$–$C_4$ mono-haloalkenyl, or $C_1$–$C_6$ alkoxyalkyl.

13. A compound as recited in claim 12 wherein $R^A$ is 2-methyl-3-thienyl or 2-methyl-3-furanyl and $Z^2$ is S.

14. A method for treating HIV infection in a patient, which comprises administering to the patient an effective amount of a compound as recited in claim 1.

15. A method for treating a HIV infection in a patient, which comprises administering to the patient an effective amount of a compound as recited in claim 2.

16. A method for treating a HIV infection in a patient, which comprises administering to the patient an effective amount of a compound as recited in claim 12.

* * * * *